(12) United States Patent
Cheshire et al.

(10) Patent No.: US 7,223,794 B2
(45) Date of Patent: May 29, 2007

(54) ARYLHETEROALKYLAMINE DERIVATIVES AND THEIR USE AS INHIBITORS OF NITRIC OXIDE SYNTHASE

(75) Inventors: David Cheshire, Loughborough (GB); Stephen Connolly, Loughborough (GB); Antonio Mete, Loughborough (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/483,163

(22) PCT Filed: Jul. 26, 2002

(86) PCT No.: PCT/SE02/01414

§ 371 (c)(1),
(2), (4) Date: Nov. 19, 2004

(87) PCT Pub. No.: WO03/011210

PCT Pub. Date: Feb. 13, 2003

(65) Prior Publication Data

US 2005/0143379 A1 Jun. 30, 2005

(30) Foreign Application Priority Data

Jul. 31, 2001 (SE) .................................. 0102640

(51) Int. Cl.
*A61K 31/275* (2006.01)
*C07C 255/07* (2006.01)
(52) U.S. Cl. ..................... 514/524; 558/422
(58) Field of Classification Search ............... 558/422; 514/524
See application file for complete search history.

(56) References Cited

U.S. PATENT DOCUMENTS

| | | | |
|---|---|---|---|
| 4,296,126 A | 10/1981 | Nedelec et al. |
| 4,314,081 A | 2/1982 | Molloy et al. |
| 4,666,910 A | 5/1987 | Schneider et al. |
| 4,902,710 A | 2/1990 | Foster et al. |
| 6,743,939 B2 | 6/2004 | Birkinshaw et al. |
| 2003/0139350 A1 | 7/2003 | Larsen et al. |

FOREIGN PATENT DOCUMENTS

| | | |
|---|---|---|
| DE | 29 07 217 A1 | 8/1979 |
| EP | 0 273 658 B1 | 7/1988 |
| EP | 0 318 727 A2 | 6/1989 |
| EP | 0 399 504 | 5/1990 |
| EP | 0 515 240 | 4/1992 |
| EP | 0 571 685 | 5/1992 |
| EP | 0 576 766 A1 | 1/1994 |
| EP | 0 661 266 | 12/1994 |
| EP | 0 707 007 | 4/1996 |
| GB | 765849 | 1/1957 |
| GB | 922600 | 4/1963 |
| GB | 1014348 | 12/1965 |
| GB | 2 060 620 A | 5/1981 |
| GB | 2 060 621 A | 5/1981 |
| GB | 2060622 | 5/1981 |
| GB | 765849 * | 1/1995 |
| JP | 51044934 B4 | 12/1976 |
| JP | 52-941 | 1/1977 |
| JP | 52000941 B4 | 1/1977 |
| WO | WO 92/19210 | 11/1992 |
| WO | WO 99/10339 | 3/1999 |
| WO | WO 99/11620 | 3/1999 |
| WO | WO 99/38514 | 8/1999 |
| WO | WO 99/62883 | 12/1999 |
| WO | WO 00/27842 | 5/2000 |
| WO | WO 00/58305 | 10/2000 |
| WO | WO 01/62704 | 8/2001 |
| WO | WO 01/62714 | 8/2001 |
| WO | WO 01/62721 | 8/2001 |
| WO | WO 02/20484 | 3/2002 |
| WO | WO 02/30899 | 4/2002 |
| WO | WO 02/090332 | 11/2002 |
| WO | WO 03/011830 | 2/2003 |

OTHER PUBLICATIONS

Chemical Abstracts, CAPLUS accession No. 1998: 394854 (Zhongguo Yaoke Daxue Xuebao, 1998, 29, 81-91).

(Continued)

*Primary Examiner*—James O. Wilson
*Assistant Examiner*—Ebenezer Sackey
(74) *Attorney, Agent, or Firm*—Fish & Richardson P.C.

(57) ABSTRACT

There are provided novel compounds of formula (I), wherein $R_1$, $R_2$, $R_3$, T, U, X, Y, V and W are as defined in the specification, and pharmaceutically acceptable salts thereof, and enantiomers and racemates thereof; together with processes for their preparation, compositions containing them and their use in therapy. The compounds are inhibitors of nitric oxide synthase and are thereby particularly useful in the treatment or prophylaxis of inflammatory disease and pain

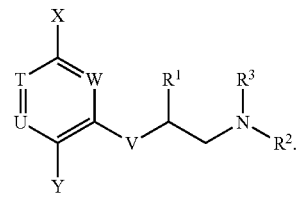

(I)

21 Claims, No Drawings

OTHER PUBLICATIONS

Chemical Abstracts, CAPLUS accession No. 1968: 28182 (J. Med. Chem., 1968, 11, 95-97).
Chemical Abstracts, CAPLUS accession No. 1997: 534782 (Zhongguo Yaoke Huaxue Zazhi, 1997, 7, 1-8).
Chemical Abstracts, CAPLUS accession No. 1999: 659361 (WO 99/51575).
Chemical Abstracts, CAPLUS accession No. 1967: 499505 (J. Chem. Soc. B, 1967, 859-866).
Chemical Abstracts, CAPLUS accession No. 1994: 579176 (Tetrahedron Letters, 1994, 35, 4585-4586).
Chemical Abstracts, CAPLUS accession No. 1968: 29366 (Probl. Poluch, Poluprod. Prom. Org. Sin., 1967, 90-97).
Chemical Abstracts, CAPLUS accession No. 1995: 664999 (DE 4 331 179).
Chemical Abstracts, CAPLUS accession No. 1995: 913361 (WO 95/15954).
Chemical Abstracts, CAPLUS accession No. 1981: 121503 (DE 2 905 877).
Chemical Abstracts, CAPLUS accession No. 1990: 35674 (JP A2 01168666).
Chemical Abstracts, CAPLUS accession No. 1978: 169760 (JP A2 52153922).
Chemical Abstracts, CAPLUS accession No. 1977: 189458 (JP B4 51044934).
Chemical Abstracts, CAPLUS accession No. 1996: 113480 (SU 1824396).
Chemical Abstracts, 1965, vol. 62, 16781 (J. Med. Chem. 1965, 8, 356-367).
Chemical Abstracts, 1958, vol. 52, 11069 (J. Am. Chem. Soc., 1958, 80, 162-164).
Chemical Abstracts, 1966, vol. 65, 2181 (Neth. Appln. 6,508,754).
Yan et al., "Potential casual prophylactic antimalarial agents. Synthesis of quinoxaline, benzimidazole, and alkoxybenzene derivatives containing a novoldiamine moiety", *J. Heterocycl. Chem.* 297-300 (1978).

* cited by examiner

ARYLHETEROALKYLAMINE DERIVATIVES AND THEIR USE AS INHIBITORS OF NITRIC OXIDE SYNTHASE

CROSS-REFERENCE TO RELATED APPLICATIONS

This application is the national phase application under 35 U.S.C. § 371 of PCT International Application No. PCT/SE02/01414, which has an International filing date of Jul. 26, 2002, and which designated Swedish Application Serial No. 0102640-0, filed Jul. 31, 2001, as priority. The contents of these applications are incorporated by reference in their entirety.

FIELD OF THE INVENTION

The present invention relates to novel arylheteroalkylamine derivatives, processes for their preparation, compositions containing them and their use in therapy.

BACKGROUND OF THE INVENTION

Nitric oxide is produced in mammalian cells from L-arginine by the action of specific nitric oxide synthases (NOSs). These enzymes fall into two distinct classes—constitutive NOS (cNOS) and inducible NOS (iNOS). At the present time, two constitutive NOSs and one inducible NOS have been identified. Of the constitutive NOSs, an endothelial enzyme (eNOS) is involved with smooth muscle relaxation and the regulation of blood pressure and blood flow, whereas the neuronal enzyme (nNOS) appears to be involved in the regulation of various biological functions. Inducible NOS has been particularly implicated in the pathogenesis of inflammatory diseases. Regulation of these enzymes should therefore offer considerable potential in the treatment of a wide variety of disease states (J. E. Macdonald, *Ann. Rep. Med. Chem.*, 1996, 31, 221–230).

Considerable effort has been expended to identify compounds that act as specific inhibitors of one or more isoforms of the enzyme nitric oxide synthase. The use of such compounds in therapy has also been widely claimed.

DISCLOSURE OF THE INVENTION

According to the present invention, there is provided a compound of formula (I)

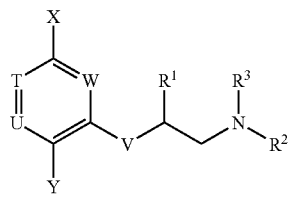

(I)

wherein:

X represents H, C1 to 4 alkyl, C1 to 4 alkoxy, halogen, OH, CN, C≡CH, $NO_2$, CHO, $COCH_3$ or NHCHO; said alkyl or alkoxy group being optionally further substituted by one or more fluorine atoms or by an OH group;

Y represents C1 to 4 alkyl, C1 to 4 alkoxy, halogen, OH, CN, CH, $NO_2$, CHO, $COCH_3$ or NHCHO; said alkyl or alkoxy group being optionally further substituted by one or more fluorine atoms;

Either one of T, U and W represents N and the other two independently represent $CR^4$; or each of T, U and W represents $CR^4$; and each $R^4$ group independently represents H, F or $CH_3$;

V represents O or $S(O)_n$;

n represents an integer 0, 1 or 2;

$R^1$ represents C1 to 4 alkyl, C2 to 4 alkenyl, C2 to 4 alhynyl, C3 to 6 cycloalkyl or a 4 to 8 membered saturated heterocyclic ring incorporating one heteroatom selected from O, S and N; any of said groups being optionally further substituted by C1 to 4 alkyl, C1 to 4 alkoxy, C1 to 4 alkylthio, C3 to 6 cycloalkyl, one or more halogens or phenyl; said phenyl group being optionally further substituted by one or more substituents selected independently from halogen, C1 to 4 alkyl, C1 to 4 alkoxy, $CF_3$, $OCF_3$, CN or $NO_2$;

or $R^1$ represents phenyl or a five or six membered aromatic heterocyclic ring containing 1 to 3 heteroatoms independently selected from O, S and N; said phenyl or aromatic heterocyclic ring being optionally substituted by one or more substituents selected independently from halogen, C1 to 4 alkyl, C1 to 4 alkoxy, OH, CN, $NO_2$ or $NR^5R^6$; said alkyl or alkoxy group being optionally further substituted by one or more fluorine atoms;

$R^2$ and $R^3$ independently represent H, C1 to 4 alkyl or C3 to 6 cycloalkyl; said alkyl group being optionally substituted by one or more groups selected independently from C1 to 4 alkoxy, halogen, OH, $NR^7R^8$, $=NR^7$, phenyl or a five or six membered aromatic or saturated heterocyclic ring containing 1 to 3 heteroatoms independently selected from O, S and N; said phenyl or aromatic heterocyclic ring being optionally further substituted by halogen, C1 to 4 alkyl, C1 to 4 alkoxy, $CF_3$, $OCF_3$, CN or $NO_2$.

$R^5$, $R^6$, $R^7$ and $R^8$ independently represent H or C1 to 4 alkyl;

or a pharmaceutically acceptable salt thereof.

It will be recognised that compounds of formula (I) wherein W represents N and X represents OH may exist in the alternative tautomeric form (Ia):

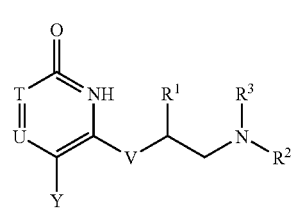

(Ia)

Analogous tautomeric structures will also exist for compounds of formula (I) wherein T represents N and X represents OH; or wherein U represents N and Y represents OH.

Compounds of formula (I) wherein $R^2$ represents H and $R^3$ represents C1 to 4 alkyl substituted on the α-carbon atom by $=NR^7$ may also exist in tautomeric forms such as those shown in formula (Ib):

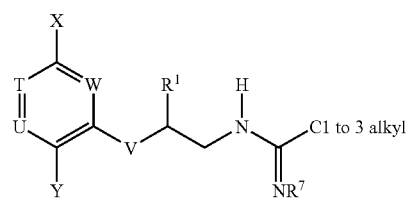

(Ib)

-continued

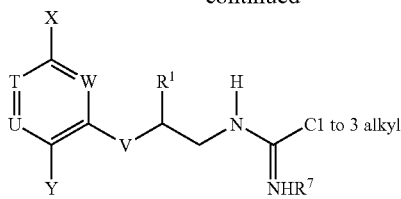

All possible tautomers of compounds of formula (I) and mixtures thereof are included within the scope of the present invention.

The compounds of formula I may exist in enantiomeric forms. All enantiomers, diastereomers, racemates and mixtures thereof are included within the scope of the invention.

The compounds of formula (I) and their pharmaceutically acceptable salts have the advantage that they are inhibitors of the enzyme nitric oxide synthase (NOS). In general, the compounds of formula (I) and their pharmaceutically acceptable salts have the advantage that they are inhibitors of the inducible isoform of the enzyme nitric oxide synthase (iNOS). Certain compounds of formula (I) and their pharmaceutically acceptable salts have the advantage that they are additionally or alternatively inhibitors of the neuronal isoform of the enzyme nitric oxide synthase (nNOS). In general, compounds of formula (I) and their pharmaceutically acceptable salts have the advantage that they show good selectivity for the inhibition of INOS and/or nNOS in comparison to the inhibition of the endothelial isoform, eNOS.

The invention further provides a process for the preparation of compounds of formula (I) or a pharmaceutically acceptable salt, enantiomer or racemate thereof.

According to the invention there is also provided a compound of formula (I), or a pharmaceutically acceptable salt thereof, for use as a medicament.

Another aspect of the invention provides the use of a compound of formula (I) or a pharmaceutically acceptable salt thereof, in the manufacture of a medicament, for the treatmentor prophylaxis of human diseases or conditions in which inhibition of nitric oxide synthase activity is beneficial.

A more particular aspect of the invention provides the use of a compound of formula (I) or a pharmaceutically acceptable salt thereof, in the manufacture of a medicament, for the treatment or prophylaxis of inflammatory disease.

Another more particular aspect of the invention provides the use of a compound of formula (I) or a pharmaceutically acceptable salt thereof, in the manufacture of a medicament, for is the treatment or prophylaxis of CNS disease.

According to the invention, there is also provided a method of treating, or reducing the risk of, diseases or conditions in which inhibition of nitric oxide synthase activity is beneficial which comprises administering to a person suffering from or at risk of, said disease or condition, a therapeutically effective amount of a compound of formula (I) or a pharmaceutically acceptable salt thereof.

More particularly, there is also provided a method of treating, or reducing the risk of, inflammatory disease in a person suffering from or at risk of, said disease, wherein the method comprises administering to the person a therapeutically effective amount of a compound of formula (I) or a pharmaceutically acceptable salt thereof.

More particularly, there is also provided a method of treating, or reducing the risk of, CNS disease in a person suffering from or at risk of, said disease, wherein the method comprises administering to the person a therapeutically effective amount of a compound of formula (I) or a pharmaceutically acceptable salt thereof.

The compounds of the present invention may also be used advantageously in combination with a second pharmaceutically active substance; particularly in combination with a cyclooxygenase inhibitor; more particularly in combination with a selective inhibitor of the inducible isoform of cyclooxygenase (COX-2). Thus, in a further aspect of the invention there is provided the use of a compound of formula (I) or a pharmaceutically acceptable salt thereof, in combination with a COX-2 inhibitor in the manufacture of a medicament for the treatment of inflammation, inflammatory disease and inflammatory related disorders. And there is also provided a method of treating, or reducing the risk of, inflammation, inflammatory disease and inflammatory related disorders in a person suffering from or at risk of, said disease or condition, wherein the method comprises administering to the person a therapeutically effective amount of a compound of formula (I) or a pharmaceutically acceptable salt thereof in combination with a COX-2 inhibitor.

In one embodiment, $R^2$ and $R^3$ independently represent H, C1 to 4 alkyl or C3 to 6 cycloalkyl; said alkyl group being optionally substituted by C1 to 4 alkoxy, halogen, OH, $NR^7R^8$, phenyl or a five or six membered aromatic or saturated heterocyclic ring containing 1 to 3 heteroatoms independently selected from O, S and N; said phenyl or aromatic heterocyclic ring being optionally further substituted by halogen, C1 to 4 alkyl, C1 to 4 alkoxy, $CF_3$, $OCF_3$, CN or $NO_2$; and X, Y, T, U, W, V, n, $R^1$, $R^2$, $R^3$, $R^4$, $R^5$, $R^6$, $R^7$ and $R^8$ are as defined above.

In one embodiment, V represents $S(O)_n$ and n represents 0.

In another embodiment, V represents O.

In another embodiment, X and Y independently represent Br, Cl, $CH_3$, $CH_2F$, $CHF_2$, $CF_3$ or CN. In yet another embodiment Y represents CN.

In another embodiment, $R^1$ represents phenyl, pyridyl, thienyl, isoxazolyl, isothiazolyl or thiazolyl. In a further embodiment, $R^1$ represents phenyl.

In one embodiment, $R^2$ represents H or $CH_3$.

In one embodiment, each $R^3$ represents H or $CH_3$.

In another embodiment, T, U and W each represent CH or CF.

In another embodiment, one of the groups T, U and W represents N, and the other two groups independently represent CH or CF. In a particular embodiment W represents N and T and U each represent CH.

In a particular embodiment, the compounds of formula (I) have the absolute stereochemistry as shown in formula (Ic):

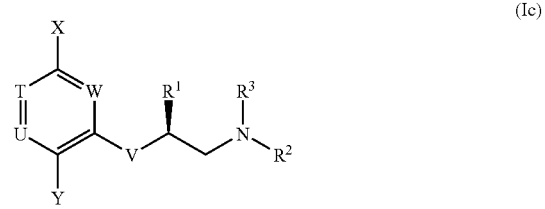

(Ic)

In one particular aspect the invention relates to compounds of formula (I) wherein V represents O or S; X and Y independently represent Br, Cl, $CH_3$, $CH_2F$, $CHF_2$, $CF_3$ or CN; $R^1$ represents phenyl, pyridyl, thienyl, isoxazolyl, isothiazolyl or thiazolyl; $R^2$ and $R^3$ each represent H or $CH_3$; T and U each represent CH or CF; W represents CH or N; and the compounds have the absolute configuration shown in formula (Ic); and pharmaceutically acceptable salts thereof.

Particular compounds of the invention include:
2-{[(1S)-2-amino-1-phenylethyl]oxy}-4-chloro-5-fluorobenzonitrile;
2-[[(1S)-2-amino-1-phenylethyl]thio]-6-methyl-3-pyridinecarbonitrile;
2-[(2,5-dichlorophenyl)thio]-2-phenylethylamine;
2-[[(1S)-2-amino-1-phenylethyl]thio]-4-chlorobenzonitrile;
N-[2-(5-chloro-2-cyano-4-fluorophenoxy)-2-phenylethyl]-ethanimidamide;
N-[2-(5-chloro-2-cyano-4-Auorophenoxy)-2-phenylethyl]-2-hydroxyethanimidade;
2-[[(1S)-2-amino-1-phenylethyl]thio]-6-(trifluoromethyl)-3-pyridinecarbonitrile;
2-[[(1S)-2-amino-1-phenylethyl]thio]-4-methoxybenzonitrile;
4-chloro-2-[[(1S)-2-(methylamino)-1-phenylethyl]thio]benzonitrile;
2-[[(1R)-2-amino-1-(3-isoxazolyl)ethyl]oxy]-4-chloro-5-fluorobenzonitrile;
2-[[2-amino-1-(3-pyridinyl) ethyl]thio]-4-chlorobenzonitrile;
and pharmaceutically acceptable salts thereof.

Unless otherwise indicated, the term "C1 to 4 alkyl" referred to herein denotes a straight or branched chain alkyl group having from 1 to 4 carbon atoms. Examples of such groups include methyl, ethyl, n-propyl, i-propyl, n-butyl, i-butyl and t-butyl.

Unless otherwise indicated, the term "C3 to 6 cycloalkyl" referred to herein denotes a cycloalkyl group having from 3 to 6 carbon atoms. Examples of such groups include cyclopropyl, cyclopentyl and cyclohexyl.

Unless otherwise indicated, the term "C2 to 4 alkenyl" referred to herein denotes a straight or branched chain alkyl group having from 2 to 4 carbon atoms incorporating at least one carbon-carbon double bond. Examples of such groups include ethenyl, propenyl and butenyl.

Unless otherwise indicated, the term "C2 to 4 alkynyl" referred to herein denotes a straight or branched chain alkyl group having from 2 to 4 carbon atoms incorporating at least one carbon-carbon triple bond. Examples of such groups include ethynyl, propynyl, and butynyl.

Unless otherwise indicated, the term "C1 to 4 alkoxy" referred to herein denotes a straight or branched chain alkoxy group having from 1 to 4 carbon atoms. Examples of such groups include methoxy, ethoxy, n-propoxy, i-propoxy and t-butoxy.

The term "C1 to 4 alkylthio" is to be interpreted analogously.

Unless otherwise indicated, the term "halogen" referred to herein denotes fluoro, chloro, bromo and iodo.

Examples of a 4 to 8 membered saturated heterocyclic ring incorporating one heteroatom selected from O, S or N include pyrrolidine, piperidine, tetrahydrofuran and perhydroazepine.

Examples of a five or six membered aromatic heterocyclic ring containing 1 to 3 heteroatoms independently selected from O, S and N include furan, thiophene, pyridine, thiazole, imidazole, oxazole, triazole, oxadiazole, thiadiazole and pyrimidine.

Examples of a five or six membered saturated heterocyclic ring containing 1 to 3 heteroatoms independently selected from O, S and N include morpholine, pyrrolidine, tetrahydrofuran, piperidine and piperazine.

Examples of a "C1 to 4 alkyl or C1 to 4 alkoxy optionally further substitutedby one or more fluorine atoms" include $CH_2F$, $CHF_2$, $CF_3$, $CF_3CF_2$, $CF_3CH_2$, $CH_2FCH_2$, $CH_3CF_2$, $CF_3CH_2CH_2$, $OCF_3$ and $OCH_2CF_3$.

According to the invention, we further provide a process for the preparation of compounds of formula (I), or a pharmaceutically acceptable salt, enantiomer or racemate thereof which comprises:
(a) reaction of a compound of formula (II)

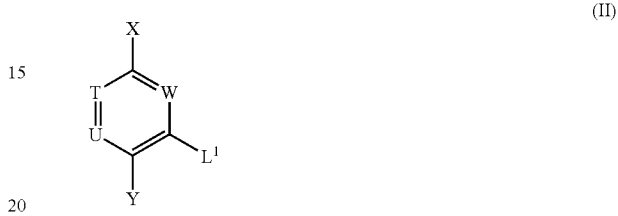

wherein T, U, X, Y and W are as defined in formula (I) and $L^1$ represents a leaving group, with a compound of formula (III)

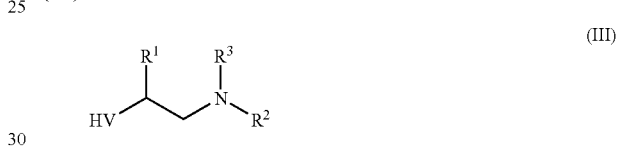

wherein $R^1$, $R^2$, $R^3$ and V are as defined in formula (I); or
(b) reaction of a compound of formula (IV)

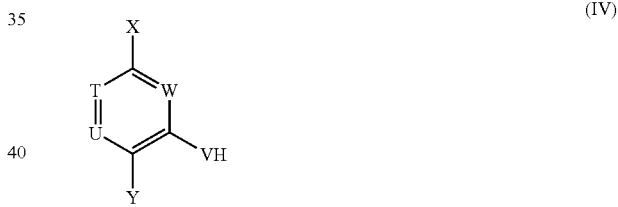

wherein T, U, W, X, Y and V are as defined in formula (I), with a compound of formula (V)

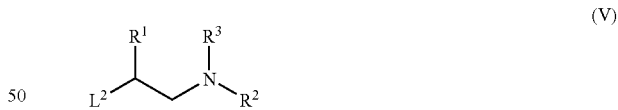

wherein $R^1$, $R^2$ and $R^3$ are as defined in formula (I) and $L^2$ is a leaving group; or
(c) reaction of a compound of formula (VI)

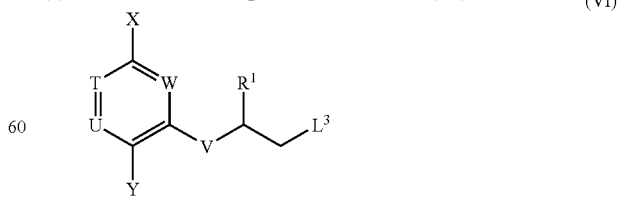

wherein $R^1$, T, U, W, X, Y and V are as defined in formula (I) and $L^3$ is a leaving group, with a compound of formula (VII)

$R^2R^3NH$ (VII)

wherein $R^2$, and $R^3$ are as defined in formula (I); or
(d) reduction of a compound of formula (VIII)

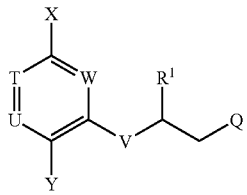
(VIII)

wherein $R^1$, T, U, W, X, Y and V are as defined in formula (I) and Q represents azide ($N_3$); or
(e) hydrolysis of a compound of formula (VIII)

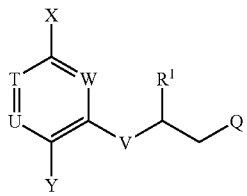
(VIII)

wherein $R^1$, T, U, W, X, Y and V are as defined in formula (I) and Q represents an imide group;

and where desired or necessary converting the resultant compound of formula (I), or another salt thereof, into a pharmaceutically acceptable salt thereof; or converting one compound of formula (I) into another compound of formula (I); and where desired converting the resultant compound of formula (I) into an optical isomer thereof.

In process (a), the reaction is performed by treating a nucleophile of formula (III) with an electrophile of formula (II) in an inert solvent. Suitable leaving groups $L^1$ include sulphonates and halides, particularly fluoride or chloride. The reaction is generally performed in the presence of a non-nucleophilic base such as sodium hydride or caesium carbonate. Suitable organic solvents are those such as N,N-dimethylformamide, N-methyl-2-pyrrolidinone, tetrahydrofuran and dimethylsulfoxide. The reaction is generally conducted at a temperature between 0° C. and the boiling point of the solvent.

In process (b), the reactants (IV) and (V) are coupled together in a suitable inert solvent such as tetrahydrofuran using, for example, Mitsunobu conditions. Thus, for example, the reactants are treated with a phosphine derivative and an azo derivative at a suitable temperature, generally between 0° C. and the boiling point of the solvent. Suitable phosphine derivatives include triphenylphosphine and tributylphosphine. Suitable azo derivatives include diethyl azodicarboxylate, diisopropyl azodicarboxylate and 1,1'-(azodicarbonyl)dipiperidine. Suitable leaving groups $L^2$ include hydroxy.

Alternatively in process (b), the reaction is performed by treating a nucleophile of formula (IV) with an electrophile of formula (V) in an inert solvent. Suitable leaving groups $L^2$ include sulphonates and halides, particularly chloride or bromide. The reaction is generally performed in the presence of a non-nucleophilic base such as sodium hydride or caesium carbonate. Suitable organic solvents are those such as N,N-dimethylformamide, N-methyl-2-pyrrolidinone, tetrahydrofuran and dimethylsulfoxide. The reaction is generally conducted at a temperature between 0° C. and the boiling point of the solvent.

In process (c), the compounds of formulae (VI) and (VII) are reacted together in a suitable inert solvent such as dimethylsulphoxide or tetrahydrofuran. The reaction is generally carried out in the presence of a base. The base may be either an added component or an excess of the amine (VII). Suitable leaving groups $L^3$ include iodide and p-toluenesulphonate.

In processes (d) and (e), the reactions are carried out using standard conditions that will be well known to the man skilled in the art.

It will be apparent to a person skilled in the art that in the above processes it may be desirable or necessary to protect an amine or hydroxyl or other potentially reactive group.

Suitable protecting groups and details of processes for adding and removing such groups may be found by reference to the standard text "Protective Groups in Organic Synthesis", 3rd Edition (1999) by Greene and Wuts.

In one preferred embodiment, amine groups are protected as carbamate derivatives, for example, as t-butyloxycarbamates.

Specific examples of the use of protecting groups are given in the Examples section.

The present invention includes compounds of formula (I) in the form of salts, in particular acid addition salts. Suitable salts include those formed with both organic and inorganic acids. Such acid addition salts will normally be pharmaceutically acceptable although salts of non-pharmaceutically acceptable acids may be of utility in the preparation and purification of the compound in question. Thus, preferred salts include those formed from hydrochloric, hydrobromic, sulphuric, phosphoric, citric, tartaric, lactic, pyruvic, acetic, succinic, fumaric, maleic, methanesulphonic and benzenesulphonic acids.

Salts of compounds of formula (I) may be formed by reacting the free base, or a salt, enantiomer or racemate thereof, with one or more equivalents of the appropriate acid. The reaction may be carried out in a solvent or medium in which the salt is insoluble or in a solvent in which the salt is soluble, for example, water, dioxane, ethanol, tetrahydrofuran or diethyl ether, or a mixture of solvents, which may be removed in vacuo or by freeze drying.

The reaction may also be a metathetical process or it may be carried out on an ion exchange resin.

Compounds of formula (III) may be prepared by reaction of a compound of formula (IX)

(IX)

wherein $R^2$ and $R^3$ are as defined in formula (I), and G represents H, Cl or $NCH_3(OCH_3)$, with an organometallic derivative, $R^1$-M, wherein $R^1$ is as defined in formula (I) and M represents a metallic residue such as lithium or magnesium-halide, followed if necessary by reduction. The resulting compound of formula (III) wherein V represents oxygen may then be subsequently converted into compounds of formula (III) wherein V represents sulphur.

Compounds of formulae (II), (IV), (V), (VI), (VIII) and (IX) are either known or may be prepared by conventional methods that will be readily apparent to the man skilled in the art.

Intermediate compounds may be used as such or in protected form. Protecting groups and details of processes for their removal may be found by reference to the standard text "Protective Groups in Organic Synthesis", 3rd Edition (1999) by Greene and Wuts.

The compounds of the invention and intermediates thereto may be isolated from their reaction mixtures and, if necessary further purified, by using standard techniques.

The compounds of formula I may exist in enantiomeric forms. Therefore, all enantiomers, diastereomers, racemates and mixtures thereof are included within the scope of the invention. The various optical isomers may be isolated by separation of a racemic mixture of the compounds using conventional techniques, for example, fractional crystallisation, or HPLC.

Intermediate compounds may also exist in enantiomeric forms and may be used as purified enantiomers, diastereomers, racemates or mixtures.

The compounds of formula (I), and their pharmaceutically acceptable salts are useful because they possess pharmacological activity in animals. In particular, the compounds are active as inhibitors of the enzyme nitric oxide synthase. More particularly, they are inhibitors of the inducible isoform of the enzyme nitric oxide synthase and as such are predicted to be useful in therapy, for example, as anti-inflammatory agents. Alternatively, they may have utility as inhibitors of the neuronal isoform of the enzyme nitric oxide synthase and as such are predicted to have utility in the treatment of CNS disorders.

The compounds and their pharmaceutically acceptable salts are indicated for use in the treatment or prophylaxis of diseases or conditions in which synthesis or oversynthesis of nitric oxide forms a contributory part. In one aspect, the compounds are indicated for use in the treatment of inflammatory conditions in mammals including man. In another aspect, the compounds are indicated for use in the treatment of CNS disorders in mammals including man.

Conditions that may be specifically mentioned are:

osteoarthitis, rheumatoid arthritis, rheumatoid spondylitis, gouty arthritis and other arritic conditions, inflamed joints;

eczema, psoriasis, dermatitis or other inflammnatory skin conditions such as sunburn;

inflammatory eye conditions including uveitis, glaucoma and conjunctivitis;

lung disorders in which inflammation is involved, for example, astbina, bronchitis, chronic obstructive pulmonary disease, pigeon fancier's disease, farmer's lung, acute respiratory distress syndrome;

bacteraeinia, endotoxaemia (septic shock), aphthous ulcers, gingivitis, pyresis, pain, meningitis and pancreatitis;

conditions of the gastrointestinal tract including inflammatory bowel disease, Crohn's disease, atrophic gastritis, gastritis varialoforme, ulcerative colitis, coeliac disease, regional ileitis, peptic ulceration, irritable bowel syndrome, reflux oesophagitis, damage to the gastrointestinal tract resulting from infections by, for example, *Helicobacter pylori*, or from treatments with non-steroidal anti-inflammatory drugs;

and other conditions associated with inflammation.

The compounds will also be useful in the treatment and alleviation of acute pain or persistent inflammatory pain or neuropathic pain or pain of a central origin.

The compounds may also be useful in the treatment of cancer.

We are particularly interested in the conditions inflammatory bowel disease, rheumatoid arthritis, osteoarthritis, chronic obstructive pulmonary disease, cancer and pain.

The compounds of formula (I) and their pharmaceutically acceptable salts may also be useful in the treatment or prophylaxis of diseases or conditions in addition to those mentioned above. For example, the compounds may be useful in the treatment of atherosclerosis, cystic fibrosis, hypotension associated with septic and/or toxic shock, in the treatment of dysfunction of the immune system, as an adjuvant to short-term immunosuppression in organ transplant therapy, in the control of onset of diabetes, in the maintenance of pancreatic function in diabetes, in the treatment of vascular complications associated with diabetes and in co-therapy with cytokines, for example TNF or interleukins.

The compounds of formula (I) may alternatively be useful in the treatment of hypoxia, for example in cases of cardiac arrest and stroke, neurodegenerative disorders including nerve degeneration and/or nerve necrosis in disorders such as ischaeinia, hypoxia, hypoglycaemia, epilepsy, and in external wounds (such as spinal cord and head injury), hyperbaric oxygen convulsions and toxicity, dementia, for example pre-senile dementia, Alzheimer's disease and AIDS-related dementia, Sydenham's chorea, Parkinson's disease, Tourette's Syndrome, Huntington's disease, Amyotrophic Lateral Sclerosis, Multiple Sclerosis, muscular dystrophy, Korsakoff s disease, imbecility relating to a cerebral vessel disorder, sleeping disorders, schizophrenia, depression, pain, autism, seasonal affective disorder, jet-lag, depression or other symptoms associated with Premenstrual Syndrome (PMS), anxiety and septic shock.

Compounds of formula (I) may also be expected to show activity in the prevention and reversal of drug addiction or tolerance such as tolerance to opiates and diazepines, treatment of drug addiction, treatment of migraine and other vascular headaches, neurogenic inflammation, in the treatment of gastrointestinal motility disorders and in the induction of labour.

We are particularly interested in the conditions stroke, Alzheimer's disease, Parkinson's disease, multiple sclerosis, schizophrenia, migraine, septic shock and pain; more particularly migraine.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

For the above mentioned therapeutic indications, the dosage administered will, of course, vary with the compound employed, the mode of administration and the treatment desired. However, in general, satisfactory results are obtained when the compounds are administered at a dosage of the solid form of between 1 mg and 2000 mg per day.

The compounds of formula (I), and pharmaceutically acceptable derivatives thereof, may be used on their own, or in the form of appropriate pharmaceutical compositions in which the compound or derivative is in admixture with a pharmaceutically acceptable adjuvant, diluent or carrier. A further aspect of the invention provides a pharmaceutical composition comprising a compound of formula (I) or a pharmaceutically acceptable salt thereof, in admixture with a pharmaceutically acceptable adjuvant, diluent or carrier. Administration may be by, but is not limited to, enteral (including oral, sublingual or rectal), intranasal, inhalation, intravenous, topical or other parenteral routes. Conventional procedures for the selection and preparation of suitable pharmaceutical formulations are described in, for example, "Pharmaceuticals—The Science of Dosage Form Designs", M. E. Aulton, Churchill Livingstone, 1988. The pharmaceutical composition preferably comprises less than 80% and more preferably less than 50% of a compound of formula (I), or a pharmaceutically acceptable salt thereof.

There is also provided a process for the preparation of such a pharmaceutical composition which comprises mixing the ingredients.

The compounds of formula (I), and pharmaceutically acceptable derivatives thereof, may also be advantageously used in combination with a COX inhibitor, more particularly in combination with a COX-2 inhibitor. Particularly preferred COX-2 inhibitors are Celecoxib and MK-966. The NOS inhibitor and the COX-2 inhibitor may either be formulated together within the same pharmaceutical composition for administration in a single dosage unit, or each component may be individually formulated such that separate dosages may be administered either simultaneously or sequentially.

The invention is illustrated, but in no way limited, by the following examples:

EXAMPLE 1

2-[[(1S)-2-Amino-1-phenylethyl]oxy]-4-chloro-5-fluorobenzonitrile (E)-butenedioate a) (S)-α-(Azidomethyl)benzenemethanol (S)-α-(Chloromethyl)benzenemethanol (2.38 g) in dry DMSO (50 ml) was treated with sodium azide (1.48 g) with stirring then heated at 60° C. for 24 h. More sodium azide (74 mg) was added and heating continued at 80° C. for a further 24 h. The reaction mixture was cooled, poured into water and extracted into ethyl acetate, which was washed with water (3×) then brine and dried ($MgSO_4$). The solvent was evaporated to give the sub-title compound (2.40 g) as a yellow oil.

$^1$H NMR 300 MHz ($CDCl_3$) 7.34–7.24 (5H, m), 4.83 (1H, m), 3.40 (2H, m).

b) 2-[[(1S)-2-Azido-1-phenylethyl]oxy]-4-chloro-5-fluorobenzonitrile

The product from step (a) (1.75 g) and 4-chloro-2,5-difluorobenzonitrile (1.86 g) in dry DMF (40 ml) were treated with 60% sodium hydride in mineral oil (470 mg) with stirring under nitrogen. The reaction mixture was stirred for 2.5 h, poured into water, and extracted with ethyl acetate. The extract was washed with water (5×) then brine and dried ($MgSO_4$). The solvent was evaporated and the residue purified by chromatography (silica, 10% ether/isohexane as eluent) to give the sub-title compound (2.37 g) as a pale yellow oil.

$^1$H NMR 300 MHz ($CDCl_3$) 7.39–7.26 (6H, m), 6.8 (1H, d), 5.24 (1H, m), 3.79 (1H, m), 3.40 (1H, dd).

c) 2-[[(1S)-2-Amino-1-phenylethyl]oxy]-4-chloro-5-fluorobenzonitrile (E)-butenedioate The product from step (b) (2.79 g) in dry THF (80 ml) was treated with triphenylphosphine (3.47 g) and water (12 ml) and the mixture heated at 60° C. for 2 h. The reaction mixture was cooled, poured into water, and extracted with ethyl acetate which was washed with water and dried ($MgSO_4$). The solvent was evaporated and the residue purified by chromatography (silica, ethyl acetate and then 10% 7M ammonia in methanol/dichloromethane as eluent) to give an oil. This was dissolved in ethanol (10 ml), treated with fumaric acid (70.3 mg) and heated until a clear solution was obtained. The mixture was evaporated and the residue triturated with ether to give after filtration and drying in vacuo the final compound (222 mg).

MS APCI+ve $^m/z$ 291 ([M+H]$^+$). $^1$H NMR 300 MHz (DMSO-$d_6$) 8.0 (1H, d), 7.54 (1H, d), 7.47–7.31 (5H, m), 6.52 (2H, s), 5.75 (1H, m), 3.21 (1H, m), 3.08 (1H, dd).

EXAMPLE 2

2-[[(1S)-2-Amino-1-phenylethyl]thio]-6-methyl-3-pyridinecarbonitrile hydrochloride a) 1,1-Dimethylethyl[(2R)-2-hydroxy-2-phenylethyl]carbamate (R)-α-(ainiomethyl)benzenemethanol (1.70 g) and bis(1,1-deimethylethyl)carbonate (2.98 g) were dissolved in methanol (20 ml) and triethylamine (4.3 ml) added. The mixture was stirred at room temperature for 4 days and then concentrated to leave the sub-title is compound as an oil (2.60 g, 88%).

$^1$H NMR 300 MHz ($CDCl_3$) 7.27–7.38 (5H, m), 4.92 (1H, m), 4.83 (1H, m), 3.50 (1H, m), 3.25 (1H, m), 1.45 (9H, s).

b) S-[(1S)-2-[[(1,1-Dimethylethoxy)carbonyl]ainino]-1-phenylethyl]benzenecarbothioate To a solution of triphenylphosphine (5.75 g) in THF (100 ml) under nitrogen at 0° C. was added diisopropylazodicarboxylate (4.55 ml) dropwise. The mixture was stirred at 0° C. for 45 minutes and then a solution of thiobenzoic acid (3.05 ml) and the product from step (a) (2.60 g) in THF (50 ml) was added dropwise at 0° C. After the addition was complete the mixture was stirred at room temperature for 0.24 h. The mixture was concentrated and the residue purified by chromatography (silica, 10% diethyl ether/isohexane as eluent) to give the sub-title compound (3.30 g, 84%) as a yellow solid.

$^1$H NMR 300 MHz ($CDCl_3$) 7.95 (2H, m), 7.56 (1H, m), 7.28–7.44 (7H, m), 4.94 (1H, m), 4.75 (1H, bs), 3.70 (2H, m), 1.38 (9H, s).

c) 1,1-Dimethylethyl [(2S)-2-[(3-cyano-6-methyl-2-pyridinyl)thio]-2-phenylethyl]carbamate To a mixture of 2-chloro-6-methyl-3-pyridinecarbonitrile (107 mg) and the product from step (b) (250 mg) in methanol (10 ml) and water (1 ml) was added potassium carbonate (200 mg). The mixture was stirred at room temperature under nitrogen for 20 h. The mixture was then concentrated, water added and extracted with ethyl acetate three times.

The organic layers were combined, washed ($MgSO_4$), dried (brine) and concentrated. The residue was purified by chromatography (silica, 20% ethyl acetate/isohexane as eluent) to give the sub-title compound (48 mg, 19%) as an oil.

MS APCI+ve $^m/z$ 370 ([M+H]$^+$).

d) 2-[[(1S)-2-Amino-1-phenylethyl]thio]-6-methyl-3-pyridinecarbonitrile hydrochloride The product from step (c) (45 mg) was dissolved in 4M HCl in dioxane (5 ml). The resulting solution was stirred at room temperature for 15 minutes, then the solvent was evaporated off. The residue was recrystallised from diethyl ether/ethanol to give the title compound as a white solid (19 mg).

MS APCI+ve $^m/z$ 270 ([M+H]$^+$). $^1$H NMR 300 MHz (DMSO-d$_6$) 8.17 (2H, bs) 8.12 (1H, d), 7.55 (2H, m), 7.38 (3H, m), 7.24 (1H, d), 5.41 (1H, t), 3.51 (2H, m), 2.61 (3H, s).

EXAMPLE 3

2-[(2,5-Dichlorophenyl)thio]-2-phenylethylamine hydrochloride a) 1,1-Dimethylethyl [2-hydroxy-2-phenylethyl]carbamate Racemic α-(aminomethyl)benzenemethanol (13.7 g) and bis(1,1-dimethylethyl)carbonate (21.8 g) were dissolved in methanol (200 ml) and 10% aqueous sodium carbonate (200 ml) added. The mixture was stirred at room temperature for 24 h, poured into 2M hydrochloric acid and extracted with ethyl acetate. Evaporation of the extract and trituration with ethyl acetate/hexane gave the sub-title compound as a pale yellow solid (27.6 g).

$^1$H NMR 300 MHz (CDCl$_3$) 7.27–7.38 (5H, m), 4.92 (1H, m), 4.83 (1H, m), 3.50 (1H, m), 3.25 (1H, m), 1.45 (9H, s).

b) 1,1-Dimethylethyl [2-[(2,5-dichlorophenyl)thio]-2-phenylethyl]carbamate

To a solution of triphenylphosphine (1.97 g), 2,5-dichlorothiophenol (0.90 g) and the product from step (a) (1.48 g) in THF (30 ml) under nitrogen at 0° C. was added diethylazodicarboxylate (1.18 ml) dropwise and the mixture was stirred at 0° C. for 45 minutes, then at room temperature for 72 h. The mixture was concentrated and the residue purified by chromatography (silica, 10% ethyl acetate/isohexane as eluent) to give the sub-title compound as a clear oil (500 mg).

$^1$H NMR 300 MHz (CDCl$_3$) 7.28 (7H, m), 7.09 (1H, dd), 4.77 (1H, bs), 4.50 (1H, bt), 3.53 (2H, m), 1.43 (9H, s).

c) 2-[(2,5-Dichlorophenyl)thio]-2-phenylethylamine hydrochloride

The product from step (b) (0.4 g) was dissolved in 4M HCl in dioxane (5 ml). The resulting solution was stirred at room temperature for 6 h, the solvent was evaporated and the residue triturated with ethyl acetate to give of the title compound (0.24 g) as, a white solid.

MS APCI+ve $^m/z$ 298/300 ([M+H]$^+$). $^1$H NMR 300 MHz (DMSO-d$_6$) 8.25 (3H, bs), 7.62 (1H, d), 7.55–7.26 (7H, m), 4.97 (1H, m), 3.45 (1H, m), 3.28 (1H, m).

EXAMPLE 4

2-[[(1S)-2-Amino-1-phenylethyl]thio]-4-chlorobenzonitrile hydrochloride a) 1,1-Dimethylethyl [(2S)-2-[(5-chloro-2-cyanophenyl)thio]-2-phenylethyl]carbamate To a solution of the product from Example 2 step (b) (360 mg) in ethanol (20 ml) was added a solution of sodium hydroxide (90 mg) in water (5 ml). After stirring for 5 minutes, 4-chloro-2-fluorobenzonitrile (156 mg) was added. The mixture was stirred at room temperature under nitrogen for 24 h. The mixture was then concentrated, water added and extracted with ethyl acetate three times. The organic layers were combined, washed (MgSO$_4$), dried and concentrated. The residue was purified by chromatography (silica, 10% diethyl ether/isohexane as eluent) to give the sub-title compound (60 mg) as an oil.

MS APCI+ve $^m/z$ 289 ([M-Boc+H]$^+$). $^1$H NMR 300 MHz (CDCl$_3$) 7.50 (1H, d), 7.43 (1H, s), 7.37–7.21 (6H, m), 4.82 (1H, bs), 4.60 (1H, t), 3.60 (2H, m), 1.42 (9H, s).

b) 2-[[(1S)-2-Amino-1-phenylethyl]thio]-4-chlorobenzonitrile hydrochloride

The title compound (34 mg) was prepared by the method of Example 2 step (d) using the product from step (a) above.

MS APCI+ve $^m/z$ 289 ([M+H]$^+$).

$^1$H NMR 300 MHz (DMSO-d$_6$) 8.18 (3H, bs), 7.88 (1H, d), 7.84 (1H, m), 7.57 (1H, dd), 7.46–7.32 (5H, m), 4.98 (1H, t), 3.51 (1H, dd), 3.33 (1H, m).

EXAMPLE 5

N-[2-(5-Chloro-2-cyano-4-fluorophenoxy)-2-phenylethyl]-ethanimidamide hydrochloride The title compound was prepared by treating the product of Example 1 step (c) (0.2 g) in dry THF (10 ml) with methyl acetimidate hydrochloride (75 mg) followed by triethylamine (0.1 ml) and stirring overnight. The reaction mixture was poured into water and extracted with ethyl acetate. The extract was evaporated and the residue purified by chromatography (silica, 2–20% 7M ammonia in methanol/dichloromethane as eluent) to give a glassy solid. The solid was dissolved in methanol (10 ml), treated with 1M HCl in ether (1 ml) then evaporated. The residue was triturated with ether to give the title compound as a cream solid (90 mg). M.p. 133–135° C.

MS APCI+ve $^m/z$ 332/334 ([M+H]$^+$). $^1$H NMR 400 MHz (DMSO-d$_6$) 9.79 (1H, bt), 9.53 (1H, bs), 8.8 (1H, bs), 8.04 (1H, d), 7.45 (6H, m), 5.84 (1H, m). 3.87 (1H, m), 3.68 (1H, m), 2.18 (3H, s).

EXAMPLE 6

N-[2-(5-Chloro-2-cyano-4-fluorophenoxy)-2-phenylethyl]-2-hydroxyethanimidamide hemi ethanedioate The title compound was prepared by the method of Example 5 using ethyl 2-hydroxyethanimidate hydrochloride in metianol and the ethanedioic acid salt of the product from Example 1 step (c). M.p. 196° C.

MS APCI+ve $^m/z$ 348 ([M+H]$^+$). $^1$H NMR 400 MHz (DMSO-d$_6$) 8.0 (1H, dt), 7.62–7.33 (6H, in), 5.84 (1H, dd), 4.17 (2H, s), 3.8 (1H, dd), 3.56 (1H, dd).

EXAMPLE 7

2-[[(1S)-2-Amino-1-phenylethyl]thio]-6-(trifluoromethyl)-3-piridinecarbonitrile a) 1,1-Dimethylethyl [(2S)-2-[[3-cyano-6-(trifluoromethyl)-2-pyridinyl]thio]-2-phenylethyl]-carbamate The sub-title compound (115 mg) was prepared by the method of Example 4 (a) using the product from Example 2 step (b) and 2-chloro-6-(trifluoromethyl)-3-pyridinecarbonitrile.

MS APCl+ve $^m$/z 324 ([M-Boc+H]$^+$). $^1$H NMR 300 MHz (CDCl$_3$) 7.94 (1H, d), 7.46–7.26 (6H, m), 5.23 (1H, t), 4.79 (1H, bs), 3.75 (2H, m), 1.39 (9H, s).

b) 2-[[(1S)-2-Amino-1-phenylethyl]thio]-6-(trifluoroimethyl)-3-pyridinecarbonitrile ethandioate The product from step (a) (110 mg) was dissolved in a solution of 4M HCl in dioxane (8 ml). The mixture was stirred at room temperature for 2 h, then evaporated to dryness. The residue was dissolved in aqueous sodium bicarbonate solution and extracted with dichloromethane (three times). The combined extracts were washed with brine, dried (MgSO$_4$) and evaporated. The residue was dissolved in ethanol and a solution of oxalic acid in ethanol added and the resultant mixture evaporated to dryness, then recrystallised from a mixture of ethanol and diethyl ether to give the title compound (85 mg) as a white solid.

MS APCl+ve $^m$/z 324 ([M+H]$^+$). $^1$H NMR 300 MHz (DMSO-d$_6$) 8.56 (1H, d), 7.87 (1H, d), 7.55 (2H, d), 7.41-7.30 (3H, m), 5.33 (1H, t), 3.65–3.48 (2H, m).

EXAMPLE 8

2-[[(1S)-2-Amino-1-phenylethyl]thio]-4-methoxybenzonitrile hydrochloride a) 1,1-Dimethylethyl [(2S)-2-[2-cyano-5-methoxyphenyl)thio]-2-phenylethyl]-carbamate The product from Example 2 step (b) (360 mg) was stirred in 7M ammonia in methanol (10 ml) for 3 h. The solvent was evaporated, the residue dissolved in dry DMF (10 ml) under nitrogen and 2-fluoro-4-methoxybenzonitrile (155 mg) added followed by caesium carbonate (655 mg). The reaction mixture was stirred under nitrogen at room temperature for 3 days then poured into water and extracted with ethyl acetate. The combined organic layers were washed with brine and dried (MgSO$_4$). The solvent was evaporated and the residue purified by chromatography (silica, 10% ethyl acetate/isohexane as eluent) to give the sub-title compound (115 mg) as an oil.

MS APCl+ve $^m$/z 285 ([M-Boc+H]$^+$). $^1$H NMR 300 MHz (CDCl$_3$) 7.50 (1H, d), 7.30 (5H, m), 6.92 (1H, s), 6.75 (1H, d), 5.30 (1H, bs), 4.59 (1H, t), 3.76 (3H, s), 3.61 (2H, m), 1.41 (9H, s).

b) 2-[[(1S)-2-Amino-1-phenylethyl]thio]-4-methoxybenzonitrile hydrochloride

The title compound (65 mg) was prepared by the method of Example 2 step (d) using the product from step (a) above.

MS APCl+ve $^m$/z 285 ([M+H]$^+$). $^1$H NMR 300 MHz (DMSO-d$_6$) 8.24 (3H, bs), 7.77 (1H, d), 7.46–7.32 (5H, m), 7.22 (1H, d), 7.01 (1H, dd), 5.01 (1H, t), 3.86 (3H, s), 3.47 (1H, m), 3.28 (1H, m).

EXAMPLE 9

4-Chloro-2-[[(1S)-2-(methylamino)-1-phenylethyl]thio]benzonitrile hydrochloride a) 1,1-Dimethylethyl [(2S)-2-[(5-chloro-2-cyanophenyl)thio]-2-phenylethyl]methylcarbamate To a solution of the product from Example 4 step (a) (92 mg) in THF (5 ml) was added sodium hydride (60% in oil; 10 mg) followed by iodomethane (60 μl). The mixture was stirred at room temperature for 2 days then poured into water and extracted with diethyl ether (three times). The combined organic layers were washed with brine and dried (MgSO$_4$). The solvent was evaporated off to give the sub-title compound (100 mg) as an oil.

MS APCl+ve $^m$/z 303 ([M-Boc+H]$^+$).

b) 4-Chloro-2-[[(1S)-2-(methylamino)-1-Rhenylethyl]thio]benzonitrile hydrochloride The title compound (30 mg) was prepared by the method of Example 2 step (d) using the product from step (a) above.

MS APCl+ve $^m$/z 303/5([M+H]$^+$). $^1$H NMR 300 MHz (DMSO-d$_6$) 7.85 (2H, m), 7.56 (1H, dd), 7.47–7.33 (5H, m), 5.10 (1H, t), 3.65 (1H, m), 3.48 (1H, m), 2.56 (3H, s).

EXAMPLE 10

2-[[(1R)-2-Amino-1-(3-isoxazolyl)ethyl]oxy]-4-chloro-5-fluorobenzonitrile ethanedioate a) (R)-2-Hydroxy-2-(3-isoxazolyl)ethylamine To ytterbium(III) chloride in acetonitrile (10 ml) was added 2,6-bis[(4S)-(−)-isopropyl-2-oxazolin-2-yl]pyridine (180 mg) and the solution stirred for 1 h. After cooling to 0° C., 3-isoxazolecarboxaldehyde (580 mg) in acetonitrile (5 ml) followed by TMSCN (0.96 ml) were added. After warming to room temperature overnight, aqueous ammonium chloride solution was added and the product extracted into diethyl ether. The extracts were dried (Na$_2$SO$_4$), the solvent was evaporated off, and the residue taken up in diethyl ether (50 ml). After cooling to 0° C., the solution was added to lithium aluimnium hydride (570 mg) in diethyl ether (10 ml) at 0° C. After 3 h at room temperature, water (0.54 ml), 15% aqueous sodium hydroxide (1.62 ml) and water (0.54 ml) were added sequentially. The mixture was filtered through celite and the solvent was evaporated off to give the sub-title compound as a yellow oil (250 mg, 40% ee).

$^1$H NMR 400 MHz (CDCl$_3$) 8.38 (1H, d), 6.43 (1H, d), 4.82 (1H, t), 3.14 (1H, dd), 3.09 (1H, dd).

b) 2-[[(1R)-2-Amino-1-(3-isoxazolyl)ethyl]oxy]-4-chloro-5-fluorobenzonitrile ethanedioate The product from step (a) (8.0 mg) in DMF (2 ml) was treated with 60% sodium hydride in mineral oil (75 mg) with stirring under nitrogen. After 30 minutes, solid 4-chloro-2,5-difluorobenzonitrile (131 mg) was added, and the reaction mixture stirred for 16 h, poured into water, and extracted with diethyl ether. The extract was washed with a mixture of brine and 1N sodium hydroxide solution (1:1) and then dried (Na$_2$SO$_4$). The solvent was evaporated off and the residue purified by passage through SCX resin (0–7M ammonia in methanol). The ethandioate salt was formed in methanol to give the title compound (6 mg) as a brown solid.

$^1$H NMR 300 MHz (CD$_3$OD) 8.79 (1H, s), 7.72 (1H, d), 7.52 (1H, d), 6.69 (1H, s), 6.01 (1H, dd), 3.77 (1H, dd), 3.60 (1H, dd).

EXAMPLE 11

2-[[2-Amino-1-(3-pyridinyl)ethyl]thio]-4-chlorobenzonitrile a) 1,1-Dimethylethyl N-[2-(methoxymethylamino)-2-oxoethyl]carbamate N,O-Dimethylhydroxylamine hydrochloride (1.95 g), EDCI (3.83 g), N-methylmorpholine (2.2 ml) and DMAP (2.44 g) were added to a solution of N-[(1,1-dimethylethoxy)carbonyl]glycine (3.5 g) in dichloromethane (60 ml)

and then stirred at room temperature for 3 days. Dichloromethane (100 ml) was added and then the solution was washed with 2M hydrochloric acid (three times), NaHCO$_3$ solution (three times) and water (three times) and then dried (MgSO$_4$). The organic layer was separated and the aqueous layer was further extracted twice. The solvent was evaporated to give the sub-title compound (3.42 g).

$^1$H NMR 300 MHz (CDCl$_3$) 5.22 (1H, bs), 4.09 (2H, d), 3.72 (3H, s), 3.46 (9H, s), 3.21 (3H, s).

b) 1,1-Dimethylethyl [2-oxo-2-(3-pyridinyl)ethyl]carbamate

Isopropylmagnesium bromide (15.5 ml, 2M in THF) was added to a solution of 3-bromopyridine (4.92 g) in THF (30 ml) at 0° C. and stirred for 1 h. A solution of the product from step (a) (2.18 g) in THF (20 ml) was then added and the reaction mixture was stirred at room temperature for 40 h. The mixture was quenched by the addition of saturated ammonium chloride solution (250 ml) and extracted with ethyl acetate. The organic layer was washed with brine and dried (MgSO$_4$). The solvent was evaporated off and the residue purified by chromatography (silica, 20% ethyl acetate/dichloromuethane as eluent) to give the sub-title compound (1.84 g) as a white solid.

MS APCI+ve$^m$/z 237 ([M+H]$^+$). $^1$H NMR 300 MHz (CDCl$_3$) 9.18 (1H, d), 8.83 (1H, q), 8.24 (1H, dd), 7.46 (1H, dd), 5.47 (1H, bs), 4.67 (2H, d), 1.48 (9H, s).

c) 1,1-Dimethylethyl [2-hydroxy-2-(3-pyridinyl)ethyl]carbamate

To a solution of the product from step (b) (1.30 g) in ethanol (50 ml) was added sodium borohydride (105 mg). The mixture was stirred for 1.5 h then evaporated. Water was added and the mixture extracted twice with ethyl acetate. The combined organic layers were washed (brine) and dried (MgSO$_4$). The solvent was evaporated off to give the sub-title compound (1.35 g) as an oil.

MS APCI+ve$^m$/z 239 ([M+H]$^+$). $^1$H NMR 300 MHz (CDCl$_3$) 8.59 (1H, m), 8.53 (1H, m), 7.73 (1H, d), 7.30 (1H, m), 4.97 (1H, bs), 4.90 (1H, m), 3.75 (1H, bs), 3.50 (1H, m), 3.30 (1H, m), 1.45 (9H, s).

d) S-[2-[[(1,1-Dimethylethoxecarbonyl]amino]-1-(3-pyridinyl)ethyl]benzenecarbothioate The sub-title compound (740 mg) was prepared by the method of Example 2 step (b) using the product from step (c) above.

MS APCI+ve$^m$/z 359([M+H]$^+$). $^1$H NMR 300 MHz (CDCl$_3$) 8.67 (1H, d), 8.53 (1H, d), 7.94 (2H, d), 7.74 (1H, d), 7.57 (1H, t), 7.45 (2H, t), 7.27 (1H, m), 4.95 (1H, t), 4.79 (1H, bs), 3.71 (2H, t), 1.38 (9H, s).

e) 1,1-Dimethylethyl [2-[(5-chloro-2-cyanophenyl)thio]-2-(3-pyridinyl)ethl]carbamate The sub-title compound (300 mg) was prepared by the method of Example 8 step (a) using oa the product from step (d) above.

MS APCI+ve$^m$/z 390/2 ([M+H]$^+$). $^1$H NMR 300 MHz (CDCl$_3$) 8.52 (2H, m), 7.73 (1H, d), 7.53 (1H, d), 7.45 (1H, s), 7.30 (2H, m), 4.85 (1H, bs), 4.63 (1H, t), 3.62 (2H, m), 1.41 (9H, s).

f) 2-[[2-Amino-1-(3-piyridinyl)ethyl]thio]-4-chlorobenzonitrile dihydrochloride

The title compound (212 mg) was prepared by the method of Example 2 step (d) using the product from step (e) above.

MS APCI+ve$^m$/z 290/2 ([M+H]$^+$). $^1$H NMR 300 MHz (DMSO-d$_6$) 8.89 (1H, s), 8.76 (1H, d), 8.43 (3H, bs), 8.31 (1H, d), 8.04 (1H, s), 7.90 (1H, d), 7.80 (1H, t), 7.64 (1H, d), 5.18 (1H, t), 3.65 (1H, m), 3.46 (1H, m).

Screens

The pharmacological activity of compounds according to the invention was tested in the following screens.

Screen 1

The activity of compounds of formula (I), or a pharmaceutically acceptable salt thereof, may be screened for nitric oxide synthase inhibiting activity by a procedure based on that of Förstermann et al., Eur. J. Pharm., 1992, 225, 161–165. Nitric oxide synthase converts $^3$H-L-arginine into $^3$H-L-citrulline which can be separated by cation exchange chromatography and quantified by liquid scintillation counting.

Enzyme is prepared, after induction, from the cultured murine macrophage cell line J774A-1 (obtained from the laboratories of the Imperial Cancer Research Fund). J774A-1 cells are cultured in Dulbeccos Modified Eagles Medium (DMEM) supplemented with 10% foetal bovine serum, 4 mM L-glutamine and antibiotics (100 units/nl penicillin G, 100 mg/ml streptomycin & 0.25 mg/ml ainphotericin B). Cells are routinely grown in 225 cm$^3$ flasks containing 35 ml medium kept at 37° C. and in a humidified atmosphere containing 5% CO$_2$.

Nitric oxide synthase is produced by cells in response to interferon-g (IFNg) and lipopolysaccharide (LPS). The medium from confluent culture flasks is removed and replaced with 25 ml (per flask) of fresh medium containing 1 mg/ml LPS and 10 units/ml IFNg. After a period of 17–20 hours in culture, harvesting of cells is accomplished by scraping the cell sheet from the flask surface into the culture medium. Cells are collected by centrifugation (1000 g for 10 minutes) and lysate prepared by adding to the cell pellet a solution containing 50 mM Tris-HCl (pH 7.5 at 20° C.), 10% (v/v) glycerol, 0.1% (v/v) Triton-X-100, 0.1 mM dithiothreitol and a cocktail of protease inhibitors comprising leupeptin (2 mg/ml), soya bean trypsin inhibitor (10 mg/ml), aprotinin (5 mg/ml) and phenylmethylsulphonyl fluoride (50 mg/ml).

For the assay, 25 µl of substrate cocktail (50 mM Tris-HCl (H 7.5 at 20° C.), 400 µM NADPH, 20 µM flavin adenine dinucleotide, 20 µM flavin mononucleotide, 4 µM tetrahydrobiopterin, 12 µM L-arginine and 0.025 mCiL-[$^3$H] arginine) is added to wells of a 96 well filter plate (0.45 µM pore size) containing 25 µl of a solution of test compound in 50 mM Tris-HCl. The reaction is started by adding 50 µl of cell lysate (prepared as above) and after incubation for 1 hour at room temperature is terminated by addition of 50 µl of an aqueous solution of 3 mM nitroarginine and 21 mM EDTA.

Labelled L-citrulline is separated from labelled L-arginine using Dowex AG-50W. 150 µl of a 25% aqueous slurry of Dowex 50W (Na$^+$ form) is added to the assay after which the whole is filtered into 96 well plates. 75 µl of filtrate is sampled and added to wells of 96 well plates containing solid scintillant. After allowing the samples to dry the L-citrulline is quantified by scintillation counting.

In a typical experiment basal activity is 300 dpm per 75 µl sample which is increased to 1900 dpm in the reagent controls. Compound activity is expressed as IC$_{50}$ (the concentration of drug substance which gives 50% enzyme inhibition in the assay) and ainlinoguanidine, which gives an IC$_{50}$ (50% inhibitory concentration) of 10 µM, is tested as a standard to verify the procedure. Compounds are tested at a range of concentrations and from the inhibitions is obtained IC$_{50}$ values are calculated. Compounds that inhibit the enzyme by at least 25% at 100 µM are classed as being active and are subjected to at least one retest.

In the above screen, the compounds of Examples 1 to 11 were tested and gave IC$_{50}$ values of less than 10 µM indicating that they are expected to show useful therapeutic activity.

Screen 2

Recombinant human NO synthases (iNOS, eNOS & nNOS) were expressed in *E. coli* and lysates were prepared in Hepes buffer (pH 7.4) containing co-factors (FAD, FMN, $H_4B$), protease inhibitors, lysozyme and the detergent, CHAPS. These preparations were used, at suitable dilution, to assess inhibition of the various isoforms. Inhibition of NOS was determined by measuring the formation of L-[$^3$H] citrulline from L-[$^3$H]argirine using an adaptation of the method of Försterrmann et al.[9] Enzyme assays were performed in the presence of 3 μM [$^3$H]arginine, 1 mM NADPH and other co-factors required to support NOS activity (FAD, FMN, $H_4B$, calmodulin, $Ca^{2+}$). Since various NOS irhibitors have been reported to exhibit slow binding kinetics, or to inactivate the enzyme in a time dependent manner, enzyme and inhibitor were pre-incubated for 60 min in the presence of NADPH before addition of arginine to initiate the reaction. Incubations continued for a further 60 min before the assays were quenched and [$^3$H]citrulline separated from unreacted substrate by chromatography on Dowex-50W resin in a 96-well format.

In the above screen, the compounds of Examples 1 to 11 were tested and gave $IC_{50}$ values of less than 10 μM against the iNOS enzyme indicating that they are expected to show useful therapeutic activity.

Screen 3

Compounds also show activity against the human form of induced nitric oxide synthase as can be demonstrated in the following assay.

The human colorectal carcinoma cell line, DLD-1 (obtained from the European Collection of Animal Cell Culture—cell line number 90102540) was routinely grown in RPMI 1640 supplemented with 10%(v/v) foetal bovine serum, and 2 mM L-glutanmine, at 37° C. in 5% $CO_2$.

Nitric oxide synthase was induced in cells by addition of medium containing human recombinant gamma-IFN (1000 units/ml), TNF-alpha (200 U/ml), IL-6 (200 U/ml) and IL-1-beta (250 U/ml). After incubation for 18 hours at 37° C., the medium was removed and the cells washed with warm phosphate buffered saline. Cells were incubated for a further 5 hours at 37° C./5% $CO_2$ in RPMI 1640 containing 100 μM L-arginine and 100 μM verapamil-HCl in the presence and absence of test compounds.

Nitrite accumulation was determined by mixing an equal volume of culture media with Griess reagent (10 mg/ml sulphanilamide, 1 mg N-(1-naphthyl)ethylenediamine in 1 ml 2.5% (v/v) phosphoric acid). Inhibition in the presence of compounds was calculated relative to the nitrite levels produced by untreated cells. $IC_{50}$ values were estimated from a semi-log plot of % inhibition versus concentration of compound.

In this screen the compounds of Examples 1 to 11 gave $IC_{50}$ values of less than 100 μM, indicating that they are predicted to show useful therapeutic activity.

The invention claimed is:

1. A compound of formula (I)

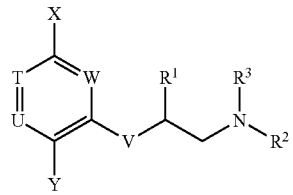

(I)

wherein:

X represents H, C1 to 4 alkyl, C1 to 4 alkoxy, halogen, OH, CN, C≡CH, $NO_2$, CHO, $COCH_3$ or NHCHO; said alkyl or alkoxy group being optionally further substituted by one or more fluorine atoms or by an OH group;

Y represents C1 to 4 alkyl, C1 to 4 alkoxy, halogen, OH, CN, C≡CH, $NO_2$, CHO, $COCH_3$ or NHCHO; said alkyl or alkoxy group being optionally further substituted by one or more fluorine atoms;

Either one of T, U and W represents N and the other two independently represent $CR^4$; or each of T, U and W represents $CR^4$; and each $R^4$ group independently represents H, F or $CH_3$;

V represents O or $S(O)_n$;

n represents an integer 0, 1 or 2;

$R^1$ represents C2 to 4 alkenyl, C2 to 4 alkynyl, C3 to 6 cycloalkyl or a 4 to 8 membered saturated heterocyclic ring incorporating one heteroatom selected from O, S and N; any of said groups being optionally further substituted by C1 to 4 alkyl, C1 to 4 alkoxy, C1 to 4 alkylthio, C3 to 6 cycloalkyl, one or more halogens or phenyl; said phenyl group being optionally further substituted by one or more substituents selected independently from halogen, C1 to 4 alkyl, C1 to 4 alkoxy, $CF_3$, $OCF_3$, CN or $NO_2$;

or $R^1$ represents phenyl or a five or six membered aromatic heterocyclic ring containing 1 to 3 heteroatoms independently selected from O, S and N; said phenyl or aromatic heterocyclic ring being optionally substituted by one or more substituents selected independently from halogen, C1 to 4 alkyl, C1 to 4 alkoxy, OH, CN, $NO_2$ or $NR^5R^6$; said alkyl or alkoxy group being optionally further substituted by one or more fluorine atoms;

$R^2$ and $R^3$ independently represent H, C1 to 4 alkyl or C3 to 6 cycloalkyl; said alkyl group being optionally substituted by one or more substituents selected independently from C1 to 4 alkoxy, halogen, OH, $NR^7R^8$, $=NR^7$, phenyl or a five or six membered aromatic or saturated heterocyclic ring containing 1 to 3 heteroatoms independently selected from O, S and N; said phenyl or aromatic heterocyclic ring being optionally further substituted by halogen, C1 to 4 alkyl, C1 to 4 alkoxy, $CF_3$, $OCF_3$, CN or $NO_2$; and $R^5$, $R^6$, $R^7$ and $R^8$ independently represent H or C1 to 4 alkyl;

or a pharmaceutically acceptable salt thereof.

2. A compound of formula (I), according to claim 1, wherein V represents O.

3. A compound of formula (I), according to claim 1, wherein V represents $S(O)_n$ and n represents O.

4. A compound of formula (I), according to claim 1, wherein X and Y independently represent Br, Cl, $CH_3$, $CH_2F$, $CHF_2$, $CF_3$ or CN.

5. A compound according to claim 4 wherein Y represents CN.

6. A compound of formula (I), according to claim 1, which is:

2-{[(1S)-2-amino-1-phenylethyl]oxy}-4-chloro-5-fluorobenzonitrile;

2-[[(1S)-2-amino-1-phenylethyl]thio]-6-methyl-3-pyridinecarbonitrile;

2-[(2,5-dichlorophenyl)thio]-2-phenylethylamine;

or a pharmaceutically acceptable salt thereof.

7. A pharmaceutical composition comprising a compound of formula (I) according to claim 1, or a pharmaceutically acceptable salt thereof, in admixture with a pharmaceutically acceptable adjuvant, diluent or carrier.

8. A method of treating, inflammatory disease in a person in need thereof, wherein the method comprises administering to the person a therapeutically effective amount of a compound of formula (I), as defined in claim 1, or a pharmaceutically acceptable salt thereof.

9. A method of treating, CNS disease in a person in need thereof, wherein the method comprises administering to the person a therapeutically effective amount of a compound of formula (I) as defined in claim 1, or a pharmaceutically acceptable salt thereof.

10. A process for the preparation of a compound of formula (I), as defined in claim 1, or a pharmaceutically acceptable salt, enantiomer or racemate thereof, wherein the process comprises:

(a) reaction of a compound of formula (II)

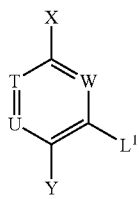

(II)

wherein T, U, X, Y and W are as defined in claim 1 and L represents a leaving group, with a compound of formula (III)

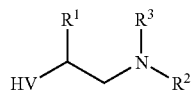

(III)

wherein $R^1$, $R^2$, $R^3$ and V are as defined in claim 1; or (b) reaction of a compound of formula (IV)

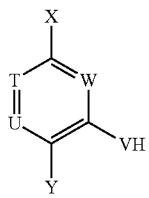

(IV)

wherein T, U, W, X, Y and V are as defined in claim 1, with a compound of formula (V)

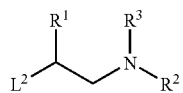

(V)

wherein $R^1$, $R^2$ and $R^3$ are as defined in claim 1 and L is a leaving group; or (c) reaction of a compound of formula (VI)

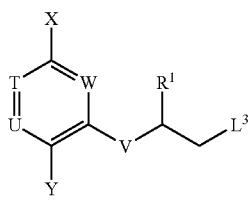

(VI)

wherein $R^1$, T, U, W, X, Y and V are as defined in claim 1 and $L^3$ is a leaving group, with a compound of formula (VII)

$R^2R^3NH$     (VII)

wherein $R^2$ and $R^3$ are as defined in claim 1; or (d) reduction of a compound of formula (VIII)

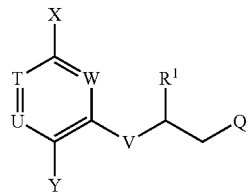

(VIII)

wherein $R^1$, T, U, W, X, Y and V are as defined in claim 1 and Q represents azide ($N_3$); or (e) hydrolysis of a compound of formula (VIII)

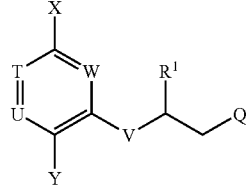

(VIII)

wherein T, U, W, X, Y and V are as defined in claim 1 and Q represents an imide group;

and where desired or necessary converting the resultant compound of formula (I), or another salt thereof, into a pharmaceutically acceptable salt thereof; or converting one compound of formula (I) into another compound of formula (I); and where desired converting the resultant compound of formula (I) into an optical isomer thereof.

11. A method of treating, inflammatory bowel disease in a person in need thereof wherein the method comprises administering to the person a therapeutically effective amount of a compound of formula (I), as defined in claim 1, or a pharmaceutically acceptable salt thereof.

12. A method of treating, rheumatoid arthritis in a person in need thereof wherein the method comprises administering to the person a therapeutically effective amount of a compound of formula (I), as defined in claim 1, or a pharmaceutically acceptable salt thereof.

13. A method of treating, osteoarthritis in a person in need thereof, wherein the method comprises administering to the person a therapeutically effective amount of a compound of formula (I), as defined in claim 1, or a pharmaceutically acceptable salt thereof.

14. A method for treating pain in a person in need thereof wherein the method comprises administering to the person a therapeutically effective amount of a compound of formula (I), as defined in claim 1, or a pharmaceutically acceptable salt thereof.

15. A method of treating, migraine in a person in need thereof, wherein the method comprises administering to the person a therapeutically effective amount of a compound of formula (I), as defined in claim 1, or a pharmaceutically acceptable salt thereof.

16. A composition comprising a compound of claim 1, in combination with a COX-2 inhibitor.

17. A method of treating an inflammatory disease, the method comprising administering to a person in need thereof a therapeutically effective amount of the composition of claim 16.

18. The compound of claim 1, wherein $R^1$ represents phenyl or a five or six membered aromatic heterocyclic ring containing 1 to 3 heteroatoms independently selected from O, S and N; said phenyl or aromatic heterocyclic ring being optionally substituted by one or more substituents selected independently from halogen, C1 to 4 alkyl, C1 to 4 alkoxy, OH, CN, $NO_2$ or $NR^5R^6$; said alkyl or alkoxy group being optionally further substituted by one or more fluorine atoms.

19. The compound of claim 1, wherein the compound is
2-[[(1S)-2-amino-1-phenylethyl]thio]-4-chlorobenzonitrile;
N-[2-(5-chloro-2-cyano-4-fluorophenoxy)-2-phenylethyl]-ethanimidamide;
N-[2-(5-chloro-2-cyano-4-fluorophenoxy)-2-phenylethyl]-2-hydroxyethanimidamide;
2-[[(1S)-2-amino-1-phenylethyl]thio]-6-(trifluoromethyl)-3-pyridinecarbonitrile;
2-[[(1S)-2-amino-1-phenylethyl]thio]-4-methoxybenzonitrile;
4-chloro-2-[[(1 S)-2-(methylamino)-1-phenylethyl]thio]benzonitrile;
2-[[(1R)-2-amino-1-(3-isoxazolyl)ethyl]oxy]-4-chloro-5-fluorobenzonitrile;
2-[[2-amino-1-(3-pyridinyl)ethyl]thio]-4-chlorobenzonitrile;
or a pharmaceutically acceptable salt thereof.

20. A pharmaceutical composition comprising a compound of formula (I) according to claim 18, or a pharmaceutically acceptable salt thereof, in admixture with a pharmaceutically acceptable adjuvant, diluent or carrier.

21. A pharmaceutical composition comprising a compound of formula (I) according to claim 19, or a pharmaceutically acceptable salt thereof, in admixture with a pharmaceutically acceptable adjuvant, diluent or carrier.

* * * * *

UNITED STATES PATENT AND TRADEMARK OFFICE
CERTIFICATE OF CORRECTION

PATENT NO.         : 7,223,794 B2
APPLICATION NO. : 10/483163
DATED                   : May 29, 2007
INVENTOR(S)       : David Cheshire, Stephen Connolly and Antonio Mete It is certified that error appears in the above-identified patent and that said Letters Patent is hereby corrected as shown below:

Column 20
Line 50, delete "O" insert -- 0 --

Column 21
Line 26, delete "L" insert -- $L^1$ --

Column 21
Line 55, delete "L" insert -- $L^2$ --

Column 22
Line 32, after "wherein" insert -- $R^1$ --

Signed and Sealed this

Twenty-sixth Day of August, 2008

JON W. DUDAS
*Director of the United States Patent and Trademark Office*